United States Patent
Franzke et al.

(10) Patent No.: US 6,328,950 B1
(45) Date of Patent: Dec. 11, 2001

(54) PIGMENT-CONTAINING FOAMABLE GEL AND DEVICE PRODUCING A FOAM FROM SAID GEL

(75) Inventors: Michael Franzke, Rossdorf; Bernd Stein, Hoesbach, both of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/448,123

(22) Filed: Nov. 24, 1999

(30) Foreign Application Priority Data

Nov. 28, 1998 (DE) .............................. 198 55 097

(51) Int. Cl.⁷ .............................. A61K 7/06; A61K 6/00; A61K 7/00; A61K 9/00
(52) U.S. Cl. ........................... 424/70.6; 424/401; 424/47; 424/70.1; 514/880; 514/944; 514/945
(58) Field of Search ........................... 424/401, 47, 70.6, 424/70.11, 45, 70.1; 514/880, 944, 945

(56) References Cited

U.S. PATENT DOCUMENTS

| 4,085,217 | * | 4/1978 | Kalopissis ........................... 514/355 |
| 5,047,230 | * | 9/1991 | Nagy et al. ........................... 424/45 |
| 5,814,309 | * | 9/1998 | Panitch ................................. 424/651 |
| 5,833,968 |   | 11/1998 | Keil et al. . |
| 5,869,032 | * | 2/1999 | Tropsch et al. ................... 424/70.15 |
| 5,876,463 | * | 3/1999 | Garcia et al. ............................ 8/405 |
| 5,879,669 | * | 3/1999 | Clausen et al. .................... 424/70.11 |

FOREIGN PATENT DOCUMENTS

| 43 15 405 A1 | 11/1994 | (DE) . |
| 298 13 861 U | 12/1999 | (DE) . |
| 0 172 713 a2 | 2/1986 | (EP) . |
| 0 172 713A2 | 2/1986 | (EP) . |
| 0 887 067 A | 12/1998 | (EP) . |

* cited by examiner

*Primary Examiner*—Dameron L. Jones
*Assistant Examiner*—Lauren Q. Wells
(74) *Attorney, Agent, or Firm*—Michael J. Striker

(57) ABSTRACT

The pigment-containing foamable gel for temporarily coloring the hair contains from 35 to 98 percent by weight water; one or more gel-forming thickener that imparts a yield point to the composition; at least one pigment; at least one film-forming, hair-fixing polymer; at least one foam-producing surfactant and at least one propellant, in combination with a suitable aerosol package and a foam-forming device for foaming the gel. The concentration of the thickener or thickeners in the gel is selected so that, on the one hand, the viscosity of the gel is sufficiently reduced so that foaming of the gel is possible and, on the other hand, the yield point is at least large enough so that settling of the pigment is prevented. The easily foamable composition has a hair-fixing effect and temporarily colors the hair, providing a high color brilliance and lustrous appearance. The composition is washable from the hair at will and the color of the hair provided by it has good fastness to rubbing.

10 Claims, No Drawings

PIGMENT-CONTAINING FOAMABLE GEL AND DEVICE PRODUCING A FOAM FROM SAID GEL

BACKGROUND OF THE INVENTION

The subject matter of the invention is a pigment-containing foam-forming gel and a device for producing a foam for temporarily coloring hair.

Production of color effects in hair is possible in many different ways. Dye precursors, which penetrate the hair and form a dyestuff there by an oxidation reaction, are used in oxidation hair dyeing compositions and methods. These dyes are permanent and cannot be washed from the hair without further effort. Other possibilities for dyeing hair include using the so-called direct-dyeing dye compounds. These direct-dyeing dye compounds are soluble organic dye compounds, which are absorbed by the hair. Dyed hair color dyed with these latter compounds is comparatively permanent and withstands several hair washings. Frequently color effects are not supposed to be permanent, but instead easily applied and similarly easily removed. One way to achieve this is the use of pigments. Pigments are insoluble colored materials, which can be deposited on the hair. Coloring effects with pigments frequently have the disadvantage that they have a reduced fastness to rubbing, i.e. a reduced friction fastness. There are a series of requirements for a pigment-containing hair treatment composition: a sufficient adherence of the pigment on the hair, as large as possible a friction fastness to mechanical rubbing, easy removability by hair washing and a high color brightness for the treated hair. Furthermore the applied treatment composition, especially when it is a matter of a styling and coloring composition, should impart good shapability and good hold to the hair. At the same time the composition should be in a pleasing and easily handled form for application.

A hair treatment composition in foam form for coloring the hair with a pigment is known from EP 0 172 713. This coloring composition is a foam-aerosol that is present in a non-viscous medium. This type of composition has the disadvantage that it must be shaken prior to use, since the undissolved pigment ingredients settle to the bottom of the aerosol container.

SUMMARY OF THE INVENTION

It is an object of the present invention to provide a gel for easily and quickly coloring hair, which is present in an easily handled form, which has a pleasing appearance and which fulfills the above-mentioned requirements while avoiding the above-described disadvantages.

It is another object of the present invention to provide a device for generating a foam for easily and quickly coloring hair, which includes an aerosol container with a foam dispenser and a foamable pigment-containing gel contained in the container.

These objects are attained according to the invention by a foamable, transparent, pigment-containing gel of the following composition.

According to the invention the pigment-containing foamable gel has the following content:

(A) from 35 to 98 percent by weight, preferably 55 to 95 percent by weight, water;

(B) at least one gel-forming thickener selected from the group consisting of thickeners that impart a yield to the composition;

(C) at least one pigment;

(D) at least one film-forming, hair-fixing polymer;

(E) at least one foam-producing surfactant; and (F) at least one propellant, advantageously in combination with a suitable aerosol package and a device for foaming the gel. The concentration of the thickeners in this gel is selected so that, on the one hand, the viscosity of the gel is sufficiently reduced so that foaming of the gel is possible and, on the other hand, the yield point is at least large enough so that settling of the pigment is prevented. Polymers that are suitable for ingredient (B) include those polymers that impart a plastic or pseudo-plastic behavior to the composition. The rheological flow properties of the gel according to the invention are characterized by the existence of a yield point, which is preferably at least 3 Pascal, measured with a Haake rotation viscometer RV 12, measuring system PKV-0.5 at 30° C. and a linearly increasing shear rate of 0 to 100 $s^{-1}$.

It is a matter of a temporary coloring-fixing composition, which fulfills the stated requirements for color brilliance, washability and friction fastness in the best way. The composition colors hair temporarily and fixes the hair at the same time. The hair resulting from treatment with this composition appears to have a high color brightness, it may appear lustrous, is washable at will and has a high friction fastness. The composition is present in a stable dispersible form with a pleasing appearance, which permits packaging in a transparent container, for example made from glass or transparent plastic, such as polyethylene terephthalate. The pigment particles are dispersed in a stable manner and do not precipitate or settle during a long storage. Thus the composition according to the invention need not be shaken to re-disperse the pigment prior to application and need not contain a ball for assisting the re-dispersal of the pigment particles. An additional advantage of the gel according to the invention is that the foam formed is stable over an exceptionally long time and however does not run off of the hair, however may be very easily worked into the hair, since it breaks down very easily when it is worked into the hair.

Preferably the gel has a measurable viscosity of 200 to 15,000 mPa s at 25° C. after exceeding the yield point. Especially the gel is a liquid gel with a viscosity of 300 to 6000, especially of 500 to 3000 mPa s at 25° C. The gel is characterized by a yield point. The yield point is selected according to the weight and surface area of the pigment particles so that it is at least as large as the pressure exerted by the pigment particles. Because of that property the pigment particles are prevented from settling.

The thickeners are preferably contained in the composition according to the invention in an amount of from 0.05 to 10 percent by weight, especially preferably from 0.1 to 4 percent by weight. The respective optimum concentration is selected according to the thickener type and the density of the pigments. Cross-linked or non-cross linked polyacrylic acid or polymethacrylic acid are suitable thickeners. Homopolymers of acrylic acid with a molecular weight of from 2,000,000 to 6,000,000, which are sold under the trademark Carbopol® of the BF Goodrich, USA, are among the thickeners that can be present in the composition according to the invention. Acrylic acid homopolymer with a molecular weight of 4,000,000 which is sold by BF Goodrich under the trademark Carbopol® can be contained in the composition according to the invention as thickener. Other thickeners include, for example, the acrylic acid homopolymer marketed by BF Goodrich under the tradename Carbopol® ETD 2001, or by Protex, France, under the trademark Modarez® V 600 PX; the copolymer made from acrylic acid and acrylamide with a molecular weight of 2,000,000 to 6,000,000 sold under the trademark Hostacerin® PN 73 by Hoechst, Germany, and the sclerotium gum sold under the trademark Amigel® by Alban Muller, Montreuil, France. Copolymers of acrylic acid or methacrylic acid, such as those sold under the trademarks Carbopol® and Pemulen® TR1 by BF Goodrich, USA, are especially preferred. Other suitable thickeners include guar gum, xanthan gum, bentonite and hectorite.

Besides the above-named thickeners, which impart a sufficient yield point to the composition, additional thickeners can be contained in the composition, which impart to the composition no sufficient yield point in the viscosity range typical for liquid gels. This type of thickeners are especially cellulose and cellulose derivative compounds, such as carboxymethtyl cellulose, cellulose ether and hydroxyalkyl celluloses, especially hydroxyethyl or hydroxypropyl cellulose.

If the thickeners contain acid groups, the acid groups are preferably at least partially neutralized with cosmetically compatible bases. Organic or inorganic bases suitable for cosmetic purposes are used as neutralization agents. Amino alcohols, such as aminomethylpropanol (AMP), triethanolamine or monoethanolamine and ammonia, NaOH and others, may be used as the bases for neutralization.

The pigments are, preferably, contained in the compositions according to the invention in an amount of from 0.01 to 25 percent by weight, especially preferably in an amount of from 5 to 15 percent by weight.

The pigments are coloring agents that are practically insoluble in the application medium and can be inorganic or organic. Also inorganic-organic mixed pigments are possible. The pigments are preferably inorganic. The advantages of inorganic pigments include outstanding light-resistance, weather-resistance and temperature resistance. The inorganic pigments can be of natural origin, for example made from chalk, ocher, umber, green earth, burnt sienna or graphite. The pigments can be white pigments, such as titanium dioxide or zinc oxide; black pigments, such as iron oxide black; many-colored pigments, such as ultramarine or iron oxide red; luster-imparting pigments, metal-effect pigments, pearlescence-imparting pigments as well as fluorescence or phosphorescent pigments. Preferably at least one pigment is a colored, non-white pigment. Metal oxides, hydroxides and oxide hydrates, mixed phase pigments, sulfur-containing silicates, metal sulfides, complex metal cyanides, metal sulfates, -chromates and -molybdates as well as metals themselves (bronze pigments) are suitable as pigments.

Titanium dioxide (Cl 77981), black iron oxide (Cl 77499), yellow iron oxide (Cl 77492), red and brown iron oxide (Cl 77491), manganic violet (Cl 77742), ultramarine (sodium aluminum sulfosilicate, Cl 77007, Pigment Blue 29), chromoxide hydrate (Cl 77289), iron blue (ferric ferrocyanide, Cl 77510) and carmine (cochineal) are especially preferred as the pigments.

Pigments based on mica which are coated with a metal oxide or a metal oxychloride, such as titanium dioxide or bismuth oxychloride, and if necessary additional color-imparting substances, such as iron oxide, iron blue, ultramarine, carmine, etc. The colors obtained with the coated pigments are determined by variation in layer thickness. This latter type of pigment includes, for example, Rona®, Colorona®, Dichrona® and Timiron® of Merck, Germany.

Suitable organic pigments in the compositions of the invention include sepia, gamboge, charcoal, Cassel brown, indigo, chlorophyll and other plant pigments. Synthetic organic pigments suitable in the composition according to the invention include azo-pigments, anthraquinonoid pigments, indigoid pigments, dioxazine pigments, quinacridone pigments, phthalocyanine pigments, isoindolinone pigments, perylene pigments and perinone pigments, metal complex pigments, alkali blue pigments and diketopyrrolopyrrol pigments.

Nanopigments are preferable as the pigments used in the compositions of the invention. The preferred particle size amounts to from 1 to 200 $\mu$m, especially 3 to 150 $\mu$m, and especially preferably 10 to 100 $\mu$m.

The gel according to the invention contains at least one synthetic or natural film-forming, hair-fixing polymer as ingredient (D). The hair-fixing polymer can be anionic, nonionic, cationic or amphoteric in character. Nonionic polymers are however especially preferred. Cationic polymers are only contained in such maximum amounts that no insoluble complexes are formed in the presence of anionic thickeners. The hair-fixing polymers can be used singly or in a mixture and are preferably in a concentration of 0.01 to 25 percent by weight, especially preferably from 0.1 to 15 percent by weight.

The film-forming hair-fixing polymers include, which when used alone in an 0.1 to 5% aqueous, alcoholic or aqueous-alcoholic situation, are in a position to deposit a polymer film on the hair and in this way to fix the hair.

Suitable natural, nonionic, film-forming polymers with a hair-fixing action include different saccharide types, such as polysaccharides or mixtures of oligo-, mono- and disaccharides, which are sold under the trademark C-PUR® of Cerestar, Brüssels, Belgium. Additional suitable natural polymers include Chinese pine rosin and cellulose derivative compounds, for example hydroxypropylcellulose with a molecular weight of 30,000 to 50,000 g/mol, which is sold for example under the trademark NISSO SL® of Lehmann & Voss, Germany.

Suitable synthetic, nonionic, film-forming hair-fixing polymers include homo- or copolymers, which are built up from monomers, which have no ionic or ionizable groups. Suitable nonionic monomers include unsaturated, radical polymerizable compounds, especially acryl- or vinyl compounds. Suitable nonionic monomers include, for example, acryl amides, methacryl amides, alkyl- and dialkylacrylamides, alkyl- and dialkylmethacrylamides, alkylacrylates, alkylmethacrylates, vinyl caprolactone, vinyl pyrrolidone, vinyl ester, vinyl alcohol, propylene glycol or ethylene glycol. The foregoing nonionic monomers preferably contain from one to seven carbon atoms, especially preferably from one to three carbon atoms.

Suitable nonionic polymers include, for example, homopolymers of vinyl pyrrolidone which for example are sold uner the trademark LUVISKOL® of BASF, Germany, or PVP-K of ISP, USA, and homopolymers of N-vinylformamide, which are sold under the trade name PVF of National Starch, USA. Additional suitable syntehtic film-forming nonionic hair-fixing polymers include, for example, the copolymerizates of vinyl pyrrolidone and vinyl acetate, which are marketed under the trademark LUVISKOL® VA of BASF, Germany; terpolymers made from vinyl pyrrolidone, vinyl acetate and vinyl propionate, which are marketed under the trademark LUVISKOL® VAP of BASF, Germany; polyacrylamides, which are marketed under the trademark AKYPOMINE® of CHEM-Y, Germany, or under the trademark SEPIGEL® 305 of SEPPIC, USA; polyvinylalcohols, which, e.g. are sold under the trademark EVANOL® of DuPont, USA, or under the trademark VINOL® 523/540 of Air Products, USA, and high molecular weight polyethylene glycol or high molecular weight copolymers of ethylene glycol with propylene glycol with fixing properties, which are sold under the trademark LIPOXOL® 100 of Hüls AG, Germany, PLURACOL E 4000 of BASF or UPIWAX® of UPI.

Polyvinylpyrrolidone, polyvinylpyrrolidone/vinyl acetate copolymer and styrene/vinyl pyrrolidone copolymer are especially preferred as nonionic polymers.

Suitable anionic hair-fixing polymers include synthetic homo- or copolymers with neutralizable monomer units containing acid groups, which are copolymerizable with comonomers, if necessary, which contain no acid groups. The acid groups may include sulfonic acid groups, phosphoric acid groups and carboxylic acid groups. Monomers containing suitable acid groups include, for example, acrylic acid, methacrylic acid, crotonic acid, maleic acid or maleic acid anhydride, aldehydocarboxylic acids or ketocarboxylic acids.

The comonomers not substituted with acid groups include, e.g., acryl amide, methacrylamides, alkyl and dialkylacrylamides, alkyl and dialkylmethacrylamides, alkylacrylates, alkylmethacrylates, vinylcaprolactone, vinylpyrrolidone, vinyl esters, vinyl alcohol, propylene glycol or ethylene glycol, amine-substituted vinyl monomers, such as dialkylaminoalkylacrylates, dialkylaminoalkylmethacrylates, monoalkylaminoalkylacrylates and monoalkylaminoalkylmethacrylates, in which the alkyl groups of these monomers preferably contain one to seven carbon atoms, especially preferably from one to three carbon atoms.

Suitable anionic polymers include homopolymers of acrylic acid or methacrylic acid that are uncross-linked or cross-linked with polyfunctional agents, copolymers of acrylic acid or methacrylic acid with monomers selected from the group consisting of acrylic acid or methacrylic acid esters, acryl amides, methacrylamides and vinylpyrrolidones, homopolymers of crotonic acid and copolymers of crotonic acid with monomers selected from the group consisting of vinyl esters, acrylic acid or methacrylic acid esters, acrylamides and methacrylamides. A suitable natural polymer is, for example, shellac.

Preferrred polymers with acid groups include cross-linked or uncross-linked vinyl acetate/crotonic acid copolymers, which, for example, are sold in the form of a 60% solution in isopropanol/water under the trademark ARISTOFLEX® of HOECHST, Germany or under the trademark LUVISET® CA-66 of BASF, Germany. Other suitable anionic polymers include, for example, terpolymers of vinyl acetate, crotonic acid and polyethylene oxide as well as terpolymers of acrylic acid, alkyl acrylate and N-alkylacrylamide, especially acrylic acid/ethyl acrylate/N-t-butylacrylamide terpolymer, as marketed under the trademark ULTRAHOLD® 8 and ULTRAHOLD® STRONG of BASF, Germany or terpolymers of vinyl acetate, crotonate and vinyl alkanoate, especially vinyl acetate/crotonate/vinyl neodecanoate copolymers, as sold under the trade name RESYN 28-2930 of National Starch.

Suitable amphoteric hair-fixing polymers include, e.g., copolymers formed from alkylacrylamides, especially octylacrylamide, alkylaminoalkylacrylates or -methacrylates and at least two monomers selected from the group consisting of acrylic acid, methacrylic acid or their esters, as sold. e.g., under the tradename AMPHOMER OR AMPHOMER LV-17 of National Starch, USA.

Suitable cationic hair-fixing polymers contain preferably quaternary or protonatable, basic amine groups. The cationic polymers can be homopolymers or copolymers, in which either the quaternary or basic nitrogen groups are part of the basic polymer chain or preferably are substituents in one or more of the monomers. The monomers containing the ammonium or amino groups can be copolymerized with non-cationic monomers. Suitable cationic monomers include unsaturated, radically polymerizable compounds, which carry at least one cationic or basic group, especially ammonium-substituted vinyl monomers, such as trialkylmethacryloxyalkyl ammonium groups, trialkylacryloxyalkyl ammonium groups, dialkyldiallyammonium groups and quaternary vinyl ammonium monomer groups with cyclic, cationic nitrogen-containing groups, such as pyridinium imidazolium or quaternary pyrrolidones, e.g. alkylvinylimidizolium, alkylvinylpyridinium or alkylvinylpyrrolidone salts. The alkyl groups of these monomers are preferably lower alkyl groups, such as alkyl groups having one to seven carbon atoms, especially preferably from one to three carbon atoms.

The monomers containing ammonium or amine groups cannot be copolymerized with non-cationic monomers. Acrylamides, methacrylamides, alkyl- and dialyklacrylamides, alkyl- and dialkylmethacrylamides, alkylacrylates, alkylmethcrylates, vinylcaprolactones, vinylcaprolactams, vinylpyrrolidones, vinyl esters, such as vinyl acetate, vinyl alcohol, propylene glycol or ethylene glycol are especially suitable as comonomers. Comonomers in which the alkylgroups have one to seven carbon atoms, especially one to three carbon atoms, are particularly preferred.

Suitable polymers with quaternary amine groups are, for example, the polymers described with the trade name Polyquaternium in the CTFA Cosmetic Ingredient Dictionary, such as methylvinylimidazolium chloride/vinylpyrrolidone copolymer (polyquaternium-16) or quaternized vinyl pyrrolidone/dimethylaminoethyl-methacrylate copolymer (polyquaternium-11) and quaternary silicone polymers or -oligomers, such as silicone polymers with quaternary terminal groups (quaternium-80).

For example, vinyl pyrrolidone/dimethylaminoethylmethacrylate methosulfate copolymer, sold under the trademark Gafquat® 755 N and Gafquat® 734 of GAF Co., USA, are suitable as a cationic polymer in the composition according to the invention. The Gafquat® 734 is especially preferred. Other cationic polymers which are suitable include, for example, the copolymer of polyvinyl pyrrolidone and imidazoliminemethochloride under the trade name LUVIQUAT® HM 550 sold by BASF, Germany; the terpolymer of dimethyldiallylammonium chloride, sodium acrylate and acrylamide sold by Calgon, USA under the trade name Merquat® Plus 3300; the terpolymer of vinyl pyrrolidone, dimethylaminoethylmethacrylate and vinyl caprolactam sold under the trademark Gaffix® VC 713 of ISP, USA; the vinyl pyrrolidone/methacrylamidopropyltrimethyl ammonium chloride copolymer sold under the trademark Gafquat® HS 100 and Gafquat® 734 of GAF Co. and the diquaternary polydimethylsiloxanes sold under the trademark Abil® Quat 3272 of GOLDSCHMIDT, Germany.

The gels according to the invention contain at least one foam-generating substance, for example a foam-producing polymer or a foam-producing surfactant, as ingredient (E). The surfactant can have a nonionic, anionic or amphoteric character. Preferably the foam-producing surfactant is nonionic. This surfactant can be used by itself or in a mixture.

The amount of surfactant can vary and is selected so that a sufficient amount of foam that can be worked into the hair when the composition is delivered from the aerosol container or from the product dispenser. The amount of surfactant present in the composition according to the invention is typically from 0.01 to 5 percent by weight, especially preferably from 0.1 to 2 percent by weight.

Suitable nonionic surfactants include, for example, $C_8$- to $C_{18}$- fatty alcohols, which can be ethoxylated with from 8 to 45 mol. ethylene oxide, e.g. lauryl-, tetradecyl-, cetyl-, oleyl- or stearyl alcohol ethoxylated with up to 40 mol. ethylene oxide per mol. fatty alcohol, alone or in a mixture; hydrogenated castor oil ethoxylated with 8 to 45 mol. ethylene oxide, $C_8$- to $C_{18}$- fatty alcohol amides; the fatty alcohols of ethoxylated lanolin or ethoxylated lanolin; polyglyceryl ethers of saturated or unsaturated fatty alcohols and alkyl phenols with 8 to 30 carbon atoms in the alkyl group and 1 to 10 glyceryl units per molecule; polyethylene/polypropylene block copolymers and ethoxylated sorbitan fatty acid esters. Derivative compounds of natural surfactants, such as alkyl polyglycosides, are especially preferred as the nonionic surfactants used in the compositions according to the invention.

Suitable anionic surfactants are, for example, alkyl sulfates, alkyl ether sulfates, alkyl sulfonates, alkoylsarcosinates, alkylisethionates or dialkylsulfosuccinates, in which the alkyl groups can contain from 8 to 18 carbon atoms.

Suitable amphoteric surfactants are especially those of the betaine type. For example, betaines include $C_8$- to $C_{18}$- alkyl betaines, such as cocodimethylcarobxymethyl betaine, lauryldimethylcarobxymethylbetaine, laurlydimethylalphacarboxyethylbetaine, cetyldimethylcarboxymethylbetaine, oleyldimethylgammacarboxypropylbetaine and lauryl-bis(2-hydroxypropyl)-alphacarboxyethylbetaine; $C_8$- to $C_{18}$- sulfobetaine, such as cocodimethylsulfopropylbetaine, stearyldimethylsulfopropylbetaine, lauryldimethylsulfoethylbetaine, lauryl-bis-(2-hydroxyethyl)sulfopropylbetaine; the carboxyl derivative of imidazole, the $C_8$- to $C_{18}$- alkyldimethylammonium acetates, $C_8$- to $C_{18}$- alkyldimethylcarboxylmethyl ammonium salts as well as $C_8$- to $C_{18}$- fatty acid alkylamidobetaines, such as the cocofattyacidamidopropylbetaine and N-cocofattyacidamidoethyl-N-[2-(carboxymethoxy)ethyl]glycerol (CTFA Name: cocoamphocarboxygylcinate).

The gels according to the invention contain at least one propellant as the ingredient (F). The propellant can be used individually or in a mixture and is preferably present in a concentration of from 2 to 40 percent by weight, especially preferably from 4 to 20 percent by weight. For example, lower alcohols, such as n-butane, i-butane, propane or their mixtures, as well as dimethylether and fluorocarbons, such as F 152 (1,1-difluoroethane) or F 134 (tetrafluoroethane) are suitable as the propellant in the compositions according to the invention. Furthermore pressurized gases, such as $N_2$, $N_2O$ and $CO_2$ and mixtures thereof are also suitable as the propellant.

The composition of the invention is packaged in a suitable pressure-tight aerosol container and has a device for foaming the composition, which permits the foaming of the gel using the propellant, as an additional component. A commercially available aerosol foam head can be used, for example, as the foam-producing device. The container is preferably made from a transparent material, through which at least the consistency and preferably the color of the composition can be observed.

The composition according to the invention is preferably packaged in an aqueous or in an aqueous-alcoholic medium. Lower alcohols suitable for cosmetic purposes with one to four carbon atoms, for example ethanol and isopropanol, can be contained in the composition as the alcohol. The water content amounts to preferably from 35 to 98 percent by weight, especially preferably from 55 to 95 percent by weight. The alcohol content preferably amounts to from 0 to 50 percent by weight, especially preferably from 0.5 to 30 percent by weight. Glycerol and propylene glycol in amounts of up to 30 percent by weight are especially preferred as additional water-soluble solvents in the composition according to the invention.

The composition according to the information can also contain conventional additive ingredients suitable for use in hair treatment compositions, for example, moisturizers; perfume oils in an amount of from 0.01 to 5 percent by weight, preservatives, bactericides and fungicides, such as 2,4,4-trichloro-2-hydroxydiphenyl ether, p-hydroxybenzoic acid or methylchloroisothiazolinone, in amounts of from 0.01 to 1.0 percent by weight; buffer substances, such as sodium citrate or sodium phosphate, in an amount of from 0.1 to 1.0 percent by weight; color-imparting substances, such as fluorescein sodium salt, in an amount of from about 0.1 to 1.0 percent by weight; care substances, such as plant and herb extracts, protein and silk hydrolyzates, lanolin derivative compounds, in an amount of from 0.1 to 5 percent by weight; light-protective agents, antioxidants, radical-trapping substances, anti-flaking substances, fatty alcohols, luster producing substances, vitamins, softeners, combability improving substances and defatting or deoiling agents, in an amount of from 0.01 to 10 percent by weight.

The composition according to the invention can be present in a pH range of from 2.0 to 9.5. The pH range from 2.5 to 8.5 is especially preferably. If the composition has a pH in the acid range, it can contain organic or inorganic acids, such as formic acid, tartaric acid, malic acid, maleic acid, fumaric acid, pyrrolidone carboxylic acid, citric acid, lactic acid, sulfuric acid, acetic acid, hydrochloric acid and phosphoric acid, among others.

The term "hair treatment" primarily means treatment of human scalp hair for the purposes of hair styling or care of the hair on the scalp.

When the composition according to the invention is used, an amount sufficient for producing the desired color effect is distributed in or on the dried hair or in or on the moist hair after the hair has been washed. The amount employed depends on the hair abundance and typically amounts to from 1 to 25 g. The composition is preferably not rinsed from the hair and remains on the hair. Subsequently the hair is combed as needed or put in a hairstyle and dried as needed. The hair styling however can occur prior to application of the composition, for example when subsequently only the curl tips, hair tips or individual strands should be colored.

The following examples illustrate the invention in further detail, but should not be considered to limit the appended claims.

EXAMPLES

Example 1

Color Mousse

| | |
|---|---|
| 6.00 g | Dichrona ® BG (Merck)[1] |
| 4.00 g | Timiron ® Starluster MP 115 (Merck)[2] |
| 2.00 g | polyvinylpyrrolidone |
| 1.80 g | 1,2-propylene glycol |
| 0.22 g | decyl glucoside |
| 0.20 g | styrene/PVP copolymer |
| 0.20 g | p-hydroxybenzoic acid methyl ester |
| 0.20 g | polyacrylic acid (Carbomer) |
| 0.18 g | PEG-40 hydrogenated castor oil |
| 0.15 g | aminomethylpropanol |
| 20.00 g | ethanol |
| 10.00 g | propanelbutane 2.7 |
| | water to 100 g |

[1]titanium dioxide/mica/ferric ferrocyanide pigment, blue luster with green shimmer
[2]mica/titanium dioxide pigment, silver luster The composition is present as a liquid gel, which is packed in a transparent PET container with a foam valve. The pigments are dispersed in a stable manner and do not settle out within a long time interval (several months). The composition may be foamed very satisfactorily. A stable, colored, voluminous foam forms on application to the hair, which does not run from the hair. It breaks up easily in the hair when it is worked into the hair..

Example 2

Color Mousse

| | |
|---|---|
| 10.00 g | Colorona Majestic Green ® (Merck)[1] |
| 1.00 g | Timiron ® Starluster MP 115 (Merck)[2] |
| 1.00 g | polyvinylpyrrolidone |
| 1.00 g | polyvinylpyrrolidone/vinyl acetate copolymer |
| 0.5 g | decyl glucoside |
| 0.4 g | phenoxyethanol |
| 6.3 g | Pemulen TR1 (BF Goodrich Chemical)[3] |
| 0.1 g | hydroxyethylcellulose |
| 0.075 g | aminomethylpropanol |
| 10.00 g | ethanol |
| 10.00 g | propane/butane 2.7 |
| | water to 100 g |

[1]titanium dioxide/mica/chromoxide green pigment, green luster
[2]mica/titanium dioxide pigment, silver luster
[3]acrylates/C 10–30 alkyl acrylates crosspolymer While the invention has been illustrated and described as embodied in a pigment-containing gel, it is not intended to be limited to the details shown, since various modifications and changes may be made without departing in any way from the spirit of the present invention.

Without further analysis, the foregoing will so fully reveal the gist of the present invention that others can, by applying current knowlege, readily adapt it for various applications without omitting features that, from the standpoint of prior art, fairly constitute essential characteristics of the generic or specific aspects of this invention.

What is claimed is new and is set forth in the following appended claims.

We claim:

1. A device for temporarily coloring hair, said device comprising
an aerosol container with a foam dispenser; and
a foamable colored gel containing from 35 to 98 percent by weight water; at least one gel-forming thickener that provides a yield point to the gel; at least one inorganic pigment; at least one film-forming, hair-fixing polymer; at least one foam-generating surfactant and at least one propellant; wherein said at least one gel-forming thickener is present in the gel in a concentration such that the gel has a sufficiently reduced viscosity so that foaming of the gel is possible and the yield point is at least large enough so that settling of the pigment is prevented, said yield point being at least 3 Pascal, measured with a Haake rotation viscometer RV 12, measuring system PKV-0.5, at 30° C. and a linearly increasing shear rate of 0 to 100 $s^{-1}$.

2. The device as defined in claim 1, wherein said aerosol container is transparent.

3. The device as defined in claim 2, wherein said aerosol container is a plastic container or a glass container.

4. The device as defined in claim 1, wherein said at least one thickener is a cross-linked or uncross-linked polyacrylic acid or polymethacrylic acid.

5. The device as defined in claim 1, wherein the gel contains from 0.05 to 10 percent by weight of said at least one gel-forming thickener.

6. The device as defined in claim 1, wherein the gel contains from 0.01 to 25 percent by weight of said at least one pigment.

7. The device as defined in claim 1, wherein the gel contains from 0.01 to 25 percent by weight of said at least one film-forming, hair-fixing polymer.

8. The device as defined in claim 1, wherein the gel contains from 0.01 to 5 percent by weight of said foam-generating surfactant.

9. The device as defined in claim 1, wherein said yield point is at least 3 Pascal, measured with a Haake rotation viscometer RV 12, measuring system PKV-0.5, at 30° C. and a linearly increasing shear rate of 0 to 100 $s^{-1}$ and the gel has a measurable viscosity of 200 to 15,000 mPa s at 25° C. after exceeding the yield point.

10. A method of temporarily coloring hair, said method comprising the steps of:

a) producing a foam for coloring the hair with a device comprising an aerosol container with a foam-forming means and a foamable colored gel contained in the aerosol container; and wherein the foamable colored gel contains from 35 to 98 percent by weight water, at least one gel-forming thickener that provides a yield point to the gel, at least one inorganic pigment, at least one film-forming, hair-fixing polymer, at least one foam-generating surfactant and at least one propellant, wherein said at least one gel-forming thickener is present in the gel in a concentration such that the gel has a sufficiently reduced viscosity so that foaming of the gel is possible and the yield point is at least large enough so that settling of the pigment is prevented, said yield point being at least 3 Pascal, measured with a Haake rotation viscometer RV 12, measuring system PKV-0.5, at 30° C. and a linearly increasing shear rate of 0 to 100 $s^{-1}$; and b) distributing a sufficient amount of the foam on the hair to achieve the desired color effect.

\* \* \* \* \*